United States Patent
Varghese et al.

(10) Patent No.: US 10,342,477 B2
(45) Date of Patent: Jul. 9, 2019

(54) LIGHT-BASED MEASUREMENT SYSTEM AND A METHOD OF COLLAGEN DENATURATION MEASUREMENT AND A SKIN TREATMENT SYSTEM

(71) Applicant: KONINKLIJKE PHILIPS N.V., Eindhoven (NL)

(72) Inventors: Babu Varghese, Eindhoven (NL); Jonathan Alambra Palero, Eindhoven (NL); Martin Jurna, Eindhoven (NL); Margaret Ruth Horton, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 255 days.

(21) Appl. No.: 15/322,748

(22) PCT Filed: Jun. 4, 2015

(86) PCT No.: PCT/EP2015/062516
§ 371 (c)(1),
(2) Date: Dec. 29, 2016

(87) PCT Pub. No.: WO2016/000902
PCT Pub. Date: Jan. 7, 2016

(65) Prior Publication Data
US 2017/0135625 A1    May 18, 2017

(30) Foreign Application Priority Data
Jul. 2, 2014   (EP) ..................................... 14175398

(51) Int. Cl.
*A61N 5/073*   (2006.01)
*A61N 5/06*    (2006.01)
(Continued)

(52) U.S. Cl.
CPC ............ *A61B 5/443* (2013.01); *A61B 5/0082* (2013.01); *A61B 5/4836* (2013.01); *A61B 18/12* (2013.01);
(Continued)

(58) Field of Classification Search
CPC ..... A61B 5/443; A61B 5/0082; A61B 5/4836; A61B 18/12; A61B 18/203;
(Continued)

(56) References Cited

U.S. PATENT DOCUMENTS 6,922,279 B2 * 7/2005 Sun ....................... G01N 21/636
                                                              356/904
9,675,415 B2 * 6/2017 Varghese ............. A61B 5/0059
(Continued)

FOREIGN PATENT DOCUMENTS

WO   WO-2006101736 A1 *   9/2006   ........... A61B 5/0059
WO       2011112248 A2    9/2011
(Continued)

OTHER PUBLICATIONS

Laubach, H.J., Tannous, Z., Anderson, R. R. and Manstein, D, "Skin responses to fractional photothermolysis", Lasers Surg. Med., 38: 142-149 (2006).
(Continued)

*Primary Examiner* — Navin Natnithithadha (57) ABSTRACT

The measurement system 110 comprises a light source 120 configured and arranged for emitting a light beam via a polarization modulator 130 to a target position inside the skin 160, wherein the polarization modulator 130 is configured and arranged to simultaneously provide, in use, a first and a second region in a cross-section of the light beam in the target position, the first and the second region being distinct and having a corresponding first and second direction of polarization, the first and the second polarization
(Continued)

direction being different from each other, and the measurement system also comprises a detection unit 150 to simultaneously detect a first and a second intensity of reflected light 145, the first intensity corresponding to light reflected from the first region of the light beam in the target position 160, and the second intensity corresponding to light reflected from the second region of the light beam in the target position 160, and the measurement system further comprises a processor being coupled to the detection unit 150 for determining a difference between the first and the second intensity.

12 Claims, 3 Drawing Sheets

(51) Int. Cl.
| | |
|---|---|
| A61B 5/00 | (2006.01) |
| A61B 18/20 | (2006.01) |
| A61B 18/12 | (2006.01) |
| G01N 21/49 | (2006.01) |
| G01N 21/63 | (2006.01) |
| A61N 1/40 | (2006.01) |
| A61N 7/00 | (2006.01) |
| A61B 17/00 | (2006.01) |
| A61B 18/00 | (2006.01) |
| A61N 5/067 | (2006.01) |

(52) U.S. Cl.
CPC .............. *A61B 18/203* (2013.01); *A61N 1/40* (2013.01); *A61N 5/0616* (2013.01); *A61N 7/00* (2013.01); *G01N 21/49* (2013.01); *G01N 21/636* (2013.01); *A61B 2017/00066* (2013.01); *A61B 2018/0047* (2013.01); *A61B 2018/00642* (2013.01); *A61N 2005/067* (2013.01); *A61N 2007/0034* (2013.01)

(58) Field of Classification Search
CPC .. A61B 2017/00066; A61B 2018/0047; A61B 2018/00642; A61N 1/40; A61N 5/0616; A61N 7/00; A61N 2005/067; A61N 2007/0034; G01N 21/49; G01N 21/636

USPC ........................................................ 600/306
See application file for complete search history.

(56) References Cited

U.S. PATENT DOCUMENTS

| | | | |
|---|---|---|---|
| 9,696,568 B2* | 7/2017 | Sakuma | ................ H01S 3/2391 |
| 2001/0056237 A1 | 12/2001 | Cane | |
| 2006/0241495 A1* | 10/2006 | Kurtz | ................... A61B 5/0059 |
| | | | 600/476 |
| 2010/0016688 A1* | 1/2010 | Debreczeny | ......... A61B 5/0059 |
| | | | 600/310 |
| 2011/0144503 A1 | 6/2011 | Debreczeny | |
| 2012/0296238 A1 | 11/2012 | Chernov | |
| 2015/0038852 A1* | 2/2015 | Debreczeny | ......... A61B 5/0059 |
| | | | 600/477 |
| 2015/0038953 A1* | 2/2015 | Varghese | ............. A61B 5/0059 |
| | | | 606/9 |
| 2015/0157253 A1* | 6/2015 | Sun | ........................ A61B 5/441 |
| | | | 600/474 |
| 2016/0270848 A1* | 9/2016 | Varghese | ............. A61B 18/203 |

FOREIGN PATENT DOCUMENTS

| | | |
|---|---|---|
| WO | 2012135961 A1 | 10/2012 |
| WO | 2013027142 A2 | 2/2013 |
| WO | 2013128330 A1 | 9/2013 |

OTHER PUBLICATIONS

Mark C Pierce, Robert L Sheridan, B Hyle Park, Barry Cense, Johannes F de Boer, "Collagen denaturation can be quantified in burned human skin using polarization-sensitive optical coherence tomography", Burns, 30(6), (2004).

Johannes F. de Boer, Shyam M. Srinivas, Arash Malekafzali, Zhongping Chen and J. Stuart Nelson "Imaging thermally damaged tissue by polarization sensitive optical coherence tomography", Optics Express, vol. 3, Issue 6, pp. 212-218 (1998) http://dx.doi.org/10.1364/OE.3.000212.

\* cited by examiner

LIGHT-BASED MEASUREMENT SYSTEM AND A METHOD OF COLLAGEN DENATURATION MEASUREMENT AND A SKIN TREATMENT SYSTEM

This application is the U.S. National Phase application under 35 U.S.C. § 371 of International Application No. PCT/EP2015/062516, filed on Jun. 4, 2015, which claims the benefit of International Application No. 14175398.8 filed on Jul. 2, 2014. These applications are hereby incorporated by reference herein.

FIELD OF THE INVENTION

This invention relates to a measurement system and a method of collagen denaturation measurement inside skin.

This invention further relates to a skin treatment system comprising the measurement system.

BACKGROUND OF THE INVENTION

The desire to maintain a youthful appearance by reducing wrinkles in the skin is an important issue in human society. Many techniques have been designed to achieve this goal. One of the techniques is, for example, skin rejuvenation, particularly methods that involve denaturation of collagen, such as thermal denaturation of collagen. Although some therapeutic applications are possible, the main area of interest is the cosmetic, or non-therapeutic, field. The efficacy of such methods in the skin depends on several factors, such as thermal and mechanical load on the tissue, age of the person undergoing the treatment, anatomical distribution of collagen inside the skin, diseases of the skin, environmental exposure, skin type, etc. At present the parameters of denaturation-based skin rejuvenation treatments are often based on trial and error.

An increasing number of these skin treatments and skin treatment systems are intended for use by consumers rather than medical professionals. These treatment systems are non-invasive—they create an effect beneath the surface of the skin without having to physically penetrate the epidermis. However, such home-use systems raise new concerns, such as concerns relating to safety and treatment efficacy. This is particularly important when the light source for performing the treatment is a laser, and incorrect operation of such a laser can result in scarring or burning of the skin at locations where the laser light passes through the skin layers.

Damage to the epidermis, for example, is highly undesirable because this may lead to complications and health risks to the person being treated, as well as social downtime. If superficial lesions are created above the dermis, petechiae (micro-bleeding) may occur due to micro-rupturing of capillaries, resulting in reduced efficacy and an increase in side effects. The formation of new collagen for the purpose of skin rejuvenation will occur if the collagen is denaturized. The efficacy of a thermal treatment for collagen denaturation, and the subsequent collagen remodeling, are high only if the temperature inside the dermis exceeds a critical temperature of 65 degrees C. At large focusing depths, the intensity in the focus may not reach the threshold required for denaturation and therefore the treatment may not produce the desired rejuvenation effects. Because the effectiveness of denaturation of collagen and the resulting skin rejuvenation depends on several factors (as indicated before), there is a need to measure the denaturation of collagen inside the skin.

Changes in the length of the collagen fibers continue during denaturation until the fibers have shrunk to a minimum length—thermal treatment beyond this phase is over-treatment because the collagen structure is completely disrupted. Over-treatment may result in unnecessary damage to surrounding tissues and other side effects without promoting any rejuvenation and tightening effect.

It is known to use the birefringence of collagen to determine the presence of collagen, and to use repeated measurements to monitor the progression of the denaturation, such as described in WO 2011/112248. Such monitoring systems may be used in combination with many different treatment methods, such as R.F. (radio frequency)-based, U.S. (ultra-sound)-based or laser-based methods. A drawback of known measurement methods is that they are relatively complex and time-consuming.

US 2011/0144503 A1 discloses a method and a system for non-invasively measuring birefringent tissues, for example collagen tissue, and changes during the treatment of such tissues, for example denaturation, by the application of RF energy. The changes are measured through linear dichroism, circular dichroism, or birefringence. The method and system optionally use polarization sensitive optical measurements to discriminate between denaturation of unidirectionally oriented strands of collagen, such as a ligament or tendon, and denaturation of planar collagen surfaces, such as the dermal layer of the skin or collagen in joint capsules.

WO 2012/135961 A1 discloses a multiphoton microscope including an excitation source for providing an optical excitation beam at an excitation wavelength $\lambda$, a scanner for scanning the excitation beam on a sample, an objective for irradiating the sample with the excitation beam scanned by the scanner and for collecting an emission beam from the sample, a first detector for detecting a plurality of multiphoton signals, and en emission light path allowing transmission from the objective to the first detector of a wavelength band limited to greater than or equal to $\lambda/2$ and less than $\lambda$, wherein the plurality of multiphoton signals have wavelengths within the wavelength band, and wherein the plurality of multiphoton signals comprise a first multiphoton signal and a second multiphoton signal of different types.

Measurement of temperature rise has the drawback that it does not provide an accurate and quantitative measure of the desired therapeutic effect, since it depends on several other factors such as age, skin optical properties and thermal properties, etc.

OBJECT OF THE INVENTION

It is an object of the invention to provide a light-based measurement system for measuring collagen denaturation and a method of collagen denaturation measurement inside the skin which are less complex.

SUMMARY OF THE INVENTION

A first aspect of the invention provides a light-based measurement system for measurement of collagen denaturation inside skin. A second aspect of the invention provides a skin treatment system comprising the measurement system according to the invention. A third aspect provides a light-based measurement method for measuring collagen denaturation inside skin.

The measurement system according to the invention comprises a light source configured and arranged for emitting a light beam; a polarization modulator configured and arranged to receive, in use, the light beam emitted by the light source and to spatially modulate a polarization direction of the light beam emitted by the light source, thereby generating a spatially modulated light beam having a spatially modulated polarization direction in a cross-section of the light beam extending perpendicularly to a propagation direction of the light beam; the measurement system being further configured and arranged to direct the spatially modulated light beam to a target position inside the skin; wherein the polarization modulator is configured and arranged to simultaneously provide, in use, at least a first and a second direction of polarization in said cross-section of the spatially modulated light beam in, respectively, at least a first and second region of the target position, the first and second regions being distinct and the first and second directions of polarization being different from each other; a detection unit configured and arranged to simultaneously detect a first and a second intensity of reflected light, the first intensity corresponding to an intensity of light reflected from the first region of the target position, and the second intensity corresponding to an intensity of light reflected from the second region of the target position; and a processor which is coupled to the detection unit and which is configured and arranged to determine a difference between the first and the second intensity.

By providing light having different polarization directions to the two or more distinct regions of the target positions, light reflected from these distinct regions will have substantially different intensities if collagen is present in the target position. If no collagen is present in the target position, or the collagen that was present in the target position has denatured sufficiently, the intensities of the light reflected from these distinct regions will be substantially identical. When the polarization direction within the monochromatic light beam is spatially varied so that distinct regions of the target position are illuminated with light having different polarization directions, the interaction of the light having the different polarization directions with collagen fibers present in the target position will be different—in other words, when the intensity measurements of the distinct regions are compared, a measured difference between the intensities of the light reflected from the distinct regions may be used to measure a degree of denaturation of the collagen present in the target position. If no substantial difference is measured between these intensities, there is either no collagen present in the target position, or the collagen in the target position has denatured below a critical detection point.

The light source may emit light which is non-polarized or polarized. The polarization modulator is selected to provide the required polarization characteristics of the incident light beam in the target position. For some embodiments, it may be advantageous when the light beam emitted by the light source is linearly polarized.

Preferably the light source is monochromatic, or only comprises a narrow spectrum of wavelengths. This may be provided by a narrow-bandwidth source, or by a monochromator in combination with a broader-bandwidth source. The measurement system is configured and arranged to provide light with a relatively narrow range of wavelengths to the target position—if necessary, a broadband polarization modulator may be used to avoid differences of the polarization direction over the range of wavelengths.

It may be also advantageous for the processor of the measurement system to be further configured to determine a degree of collagen denaturation using the difference between the first and second intensity. Although the detection of a difference may give a suitable signal in many cases, a more complex system in which the current measurement is compared to earlier measurements may be used to determine the degree of denaturation.

Additionally, simultaneous measurements at a plurality of target positions in the skin may further increase the reliability of the system.

Additionally, the processor may be provided with additional detailed information, such as information concerning the person or region being treated, or the treatment. For example, information about age, skin color, stage in the treatment, position of the target positions and intensity measurement positions on the body may be used by the processor to determine the degree of collagen denaturation.

It may also be advantageous when the light beam emitted by the light source is linearly polarized, and in particular when the measurement system is configured and arranged such that the first and the second direction of polarization each comprise a linear polarization, and an angular difference between the first and the second direction of polarization is approximately equal to 45 degrees.

When the linearly polarized light interacts with birefringent collagen structures, the intensity of backscattered light detected depends on the relative orientation of the polarization direction of the incident light and the direction of the collagen fibers. Birefringence causes the orthogonal components of the electric field of the incident light to experience different refractive indices when the plane of polarization of the incident light is not parallel or perpendicular to the optical axis of the collagen fibres. In other words, the intensity of the reflected light will be at a minimum when the angle ($\theta$) between the polarization direction of the incident light and the collagen fiber orientation is approximately 0 or 90 degrees. The intensity of the reflected light will be at a maximum when the angle ($\theta$) between the polarization direction of the incident light and the collagen fiber orientation is approximately 45 degrees. Because, in this embodiment, the angular difference between the first and the second direction of polarization in the incident light beam is equal to 45 degrees, the difference between the first and second intensities of the reflected light will be at a maximum.

In target positions inside the skin in which a concentration of collagen fibers is relatively high, the difference between the first and second intensities of the reflected light will also be relatively high.

Because the polarization directions of the light in the first and second regions in the target position is predetermined, and because the measurement of the difference between the first and the second intensity of the reflected light is performed simultaneously, the measurement system provides a relatively simple and stable way of light-based measurement of the collagen concentrations and collagen denaturation as compared to the known methods. This makes it simpler to integrate the measurement system into a skin treatment device, and repeated measurements will provide a more accurate monitoring of the collagen denaturation.

The detection unit may comprise two or more photon detectors, each photon detector being configured and arranged to measure the intensity of the light reflected from a respective one of the first and second regions of the target position. The photon detectors may be relatively simple photodiodes or any other detectors able to detect the intensity of the reflected light. In an embodiment, the detection unit may, for example, comprise an array of detectors, such as a CCD array, and the processor may be configured and arranged to compare the intensities measured by distinct areas of the array to determine the difference between the intensities of the light reflected from the first and second regions.

In an embodiment of the measurement system, the measurement system further comprises an optical element for focusing the spatially modulated light beam into the target position inside the skin. A benefit of this embodiment is that the focused light limits the dimensions of the target position inside the skin where the measurement is performed, thereby further improving the quality of the measurement as well as the detection of the collagen fibers that have denaturized.

In an embodiment of the measurement system, the first and the second intensity detected by the detection unit correspond to an intensity of a second harmonic generated light (SHG) component reflected from, respectively, the first and the second region of the target position. Typically, measuring the second harmonic generated light reflected from the target position inside the skin will significantly increase the signal-to-noise ratio of the measured intensity differences and thus increase the reliability of the collagen measurement inside the skin.

The detection of a generated second harmonic light component to detect the presence of collagen is known from, for example, published Japanese patent application JP 2009/236610 A.

In an embodiment of the measurement system, the detection unit comprises a harmonic separator for separating the reflected second harmonic generated light component from the light beam emitted by the light source. The harmonic separator basically blocks light reflected from the target position inside the skin having the same wavelengths as the light emitted by the light source, such that the light originally emitted by the light source does not reach the detection unit. By ensuring that only the second harmonic generated light reaches the detection unit the signal-to-noise ratio is significantly enhanced.

In an embodiment of the measurement system, a wavelength of the light beam emitted by the light source is in a range from visible light to infrared light. The wavelength range may comprise wavelengths between 400 and 2000 nanometer. A suitable infrared wavelength, for which relatively high-intensity light sources are commercially available, is 1064 nanometer, which is widely used, for example, in glass-fiber communication networks. High-intensity laser diodes emitting light of 1064 nanometer can relatively suitably be used in the measurement system according to the invention, because these laser-diodes generate a relatively high intensity, and are nevertheless relatively small. In addition, this wavelength provides a relatively good penetration depth of the emitted light into the skin. For a 1064 nanometer light source, the light reflected from the birefringent collagen fibers will include the second harmonic generated (SHG) light having a wavelength of 532 nanometer. This reflected SHG light may be relatively easily detected by means of a vast range of detection units—including standard commercially available CCD-sensors (cameras)—as the reflected light is within the visible range of the optical spectrum.

The skin treatment system according to a further aspect of the invention comprises the measurement system according to the invention.

In an embodiment of the skin treatment system, the measurement system is configured for measuring the difference between the first and the second intensity before and after a denaturation treatment by the skin treatment system, or for measuring the difference between the first and the second intensity during the denaturation treatment by the skin treatment system, to thereby monitor efficacy or progress of the denaturation treatment. Again, as indicated before, the measurement system may be used as a real-time measurement system for measuring the efficacy of the denaturation treatment. When, for example, the intensity difference before and after the denaturation treatment has not changed significantly, or when the intensity difference during the denaturation treatment does not change significantly, the denaturation process may not occur or may occur at a very slow rate. This may be caused by, for example, the fact that the intensity of the emitted light beam is too low, or by the fact that all collagen fibers present in the target position inside the skin have already been denaturized such that the denaturation treatment does not significantly change the denaturation state of the collagen. Due to the relatively simple and fast measurement of the collagen fiber denaturation condition by means of the measurement system according to the invention, real-time measurement may be done and the treatment may be stopped or changed when the treatment appears to be not effective enough. This will prevent skin damage due to, for example, excessive treatments and will increase the effectiveness of the overall treatment.

The collagen denaturation treatment may, for example, be performed by means of a focused treatment source, for example, an RF energy source or an Ultrasound source or, for example, a laser source providing treatment light. The measurement system may, for example, measure the denaturation process in real-time during the operation of the RF energy source or the laser source providing the treatment. During the treatment, the length of the collagen fibers is reduced until the fibers have shrunk to a critical length. Beyond this critical length, denaturation treatment is not effective anymore for further rejuvenation as the collagen structure is completely disrupted at this stage. The intensity difference measured by the measurement system during the treatment will gradually decrease and may, for example, stabilize at a substantially zero difference, which indicates that further treatment is not effective and preferably should be discontinued to avoid adverse side effects such as skin damage.

The invention further relates to a method of collagen denaturation measurement inside skin, the method comprising steps analogous to the features and functions comprised in the measurement system. The measurement system described above is, in fact, configured and arranged to perform this method.

These and other aspects of the invention are apparent from and will be elucidated with reference to the embodiments described hereinafter.

DETAILED DESCRIPTION OF THE INVENTION

Figure 1:
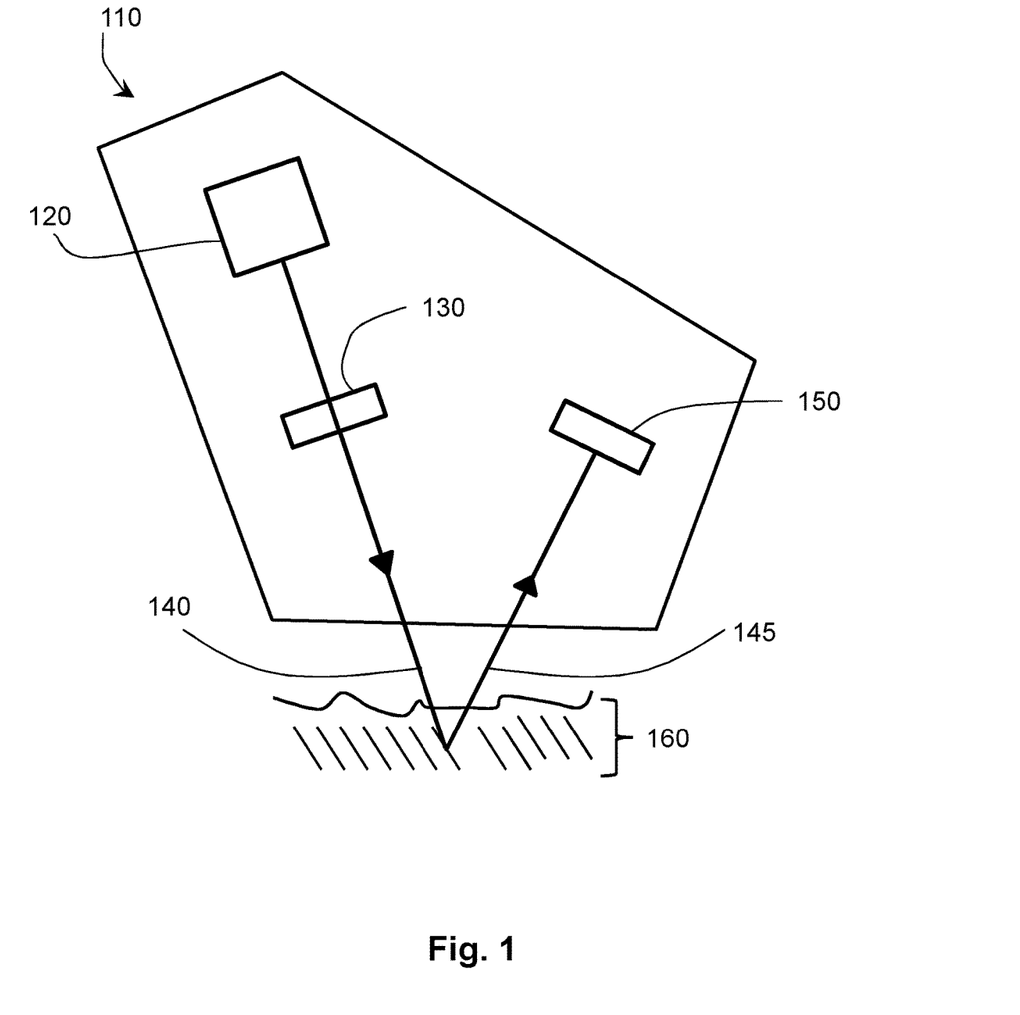
FIG. 1 schematically shows a measurement system according to the invention.

FIG. 1 schematically shows a skin measurement system 110 according to the invention. The measurement system 110 is configured and arranged for performing light-based measurement of collagen denaturation inside the skin 160. The measurement system 110 comprises a light source 120 for emitting light via a polarization modulator 130 to a target position inside the skin 160. The light source 120 is preferably a monochromatic source, such as laser or laser diode. A light source 120 with a narrow wavelength range may also be used.

The polarization modulator 130 is configured and arranged to receive, in use, the light beam emitted by the light source 120, and to spatially modulate a polarization direction of the light beam emitted by the light source, thereby generating a spatially modulated light beam having a spatially modulated polarization direction in a cross-section of the light beam extending perpendicularly to a propagation direction of the light beam. Thus, the polarization modulator 130 provides, within the incident light beam 140, two or more areas of different polarization directions in said cross-section of the light beam, which are incident on an outer layer of skin during use.

The light source 120 is configured and arranged such that the light emitted may penetrate through the outer layer of skin to reach the target position inside the skin.

The polarization modulator 130 is configured and arranged to simultaneously provide, in use, at least a first and a second direction of polarization in said cross-section of the spatially modulated light beam in, respectively, at least a first and a second region of the target position. Thus, the polarization modulator 130 is configured and arranged to simultaneously provide, in use, two or more distinct regions in the cross-section of the light beam in the target position, in which distinct regions the polarization of the light has significantly different directions or orientations. The regions are distinct—in other words, they may be adjacent, separate or they may even partially coincide, on the proviso that the measurement system can measure an intensity of the light reflected by each distinct region such that a difference in the intensity may be distinguished.

During use, light is reflected from the target position. The measurement system 110 further comprises a detection unit 150 for detecting a first and second intensity of reflected light 145, the first intensity corresponding to light reflected from the first region of the target position 160, and the second intensity corresponding to light reflected from the second region of the target position 160. The first and second intensity represent the reflection of the incident light beam 140 by, respectively, the first and second regions of the target position.

In the measurement system 110, a processor is coupled to the detection unit 150, and configured and arranged to simultaneously determine a difference in intensity between the first and second intensities.

Additional optical elements known in the art may also be provided to further guide, and modify, the incident light beam 140 to the target position inside the skin 160, and to further guide and modify the reflected light beam 145 from the target position.

During use, the measurement system 110 is brought into proximity of an outer layer of skin 160. The system 110 illuminates the target position with two or more regions of polarized light—these regions are distinct and have a respective first and second direction of polarization, the polarization directions of the first and second regions being substantially different from each other. The polarization directions and the disposition of the regions are determined mainly by the configuration and arrangement of the polarization modulator 130.

The invention is based on the insight that known techniques of collagen detection, such as disclosed in WO2013128330, may be simplified. It is well known that collagen is a birefringent tissue constituent, and the birefringence ($\Delta n$) is estimated to be $2.8 \times 10\text{-}3\text{-}3.0 \times 10\text{-}3$. When linearly polarized light interacts with birefringent collagen structures, the intensity of backscattered light detected depends on the relative orientation of the incident polarization with respect to the collagen fibers.

Known techniques of collagen detection require polarization rotators to better control the polarization of the light incident on or reflected from the collagen fibers to improve collagen detection. In addition, measurements must be repeated with the different polarization settings.

In the invention, the target position is illuminated with at least two distinct regions of polarized light having polarization directions which are substantially different from each other. The intensity of the reflected light from these two regions is measured simultaneously, and a difference between the intensities of the light reflected from the two regions indicates the presence of collagen in the target position.

The skilled person may use any spatially-varying polarization modulator 130 known in the art to simultaneously provide, in use, at least a first and a second direction of polarization in a cross-section of the spatially modulated light beam in suitable regions at the target position. In this context, the expression "modulator" may be understood as one or more optical components which work together to selectively transmit the required polarizations, or to modify the light characteristics to obtain the required polarizations, or some combination of filtering and modifying.

A spatially-varying or spatially-modulated polarized light beam may be understood as a light beam having a cross-section in which different positions in the cross-section have different polarization directions.

Figure 3A:
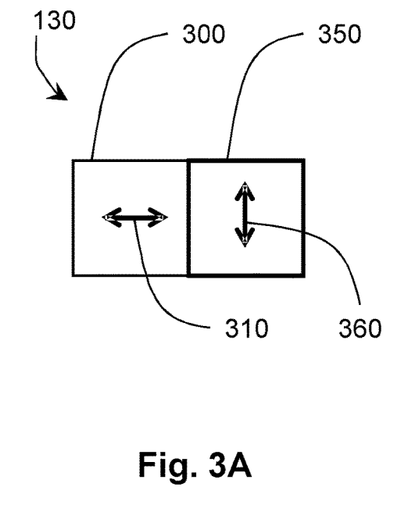

FIG. 3A schematically depicts an example of a polarization modulator 130. It has two segments 300, 350—the first segment provides linear polarization direction 310 in the left-to-right direction (as schematically depicted) and the second segment provides linear polarization direction 360 in the up-to-down direction (as schematically depicted). To use the modulator of FIG. 3A, the measurement system 110 is configured and arranged such that the polarization modulator 130 provides areas in a beam cross-section with a predetermined or controlled polarization direction.

For example, the modulator 130 of FIG. 3A may be transmissive and placed such that it intersects the light beam between the light source 130 and the target position inside the skin 160. Each segment 300, 350 provides distinct areas in a beam cross-section with a substantially different polarization direction. In this example, the areas are adjacent. For the invention, it is the difference in polarization direction or orientation that mainly determines the sensitivity and accuracy of the collagen denaturation measurement. In this case, the areas in a beam cross-section have polarization directions which differ by 90 degrees. The measurement system 110 will correspondingly provide distinct regions of the target position with polarization directions which differ by 90 degrees. In this example, the regions are also adjacent. The polarization direction of the incident light in a first region will correspond to the direction provided by the first segment 300, and the polarization direction of the incident light in a second region will correspond to the direction provided by the second segment 350.

Such a polarization modulator 130 may be manufactured by cutting known transmissive polarization filters into segments of suitable size and bringing these segments in proximity of the required relative polarization orientation. Suitable selection of waveplates and SVR's (Spatially Varying Retarders)—either individually or in combination—may also be used.

As the skilled person will be aware, the same distinct regions of different polarization in the target area may be achieved by using a reflective polarization modulator 130, such as an LCOS (Liquid Crystal On Silicon) element. In some embodiments, a combination of transmissive and reflective optical elements may also be advantageous.

Figure 3B:
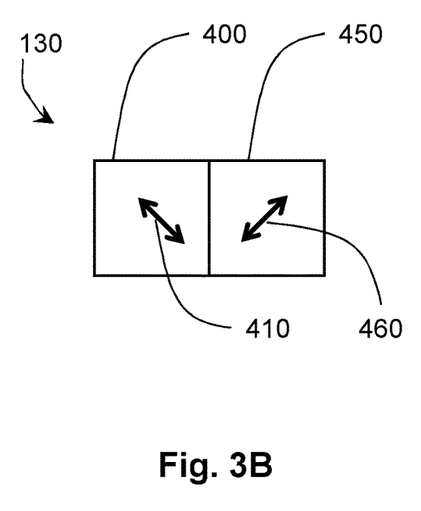

Similarly, FIG. 3B depicts schematically a further polarization modulator which may be provided using transmissive and/or reflective optical components. It comprises two distinct and adjacent segments 400, 450. The first segment 400 provides an area in a beam cross-section with a linear polarization direction 410 in the top left-to-bottom right direction (as schematically depicted) and the second segment provides linear polarization direction 340 in the top right-to-bottom left direction (as schematically depicted). As in FIG. 3A, the areas in a beam cross-section have polarization directions which differ by 90 degrees, and the corresponding regions in the target area in the skin will also comprise light with polarization directions which differ by 90 degrees.

The measurement system 110 detects a first intensity associated with light reflected 145 from the first region and simultaneously detects a second intensity associated with light from the second region. The presence of collagen will result in a difference in intensity between the first and second intensity measurements. The skilled person may use trial and error to determine the most appropriate position in each region to measure the intensity.

Figure 3C:
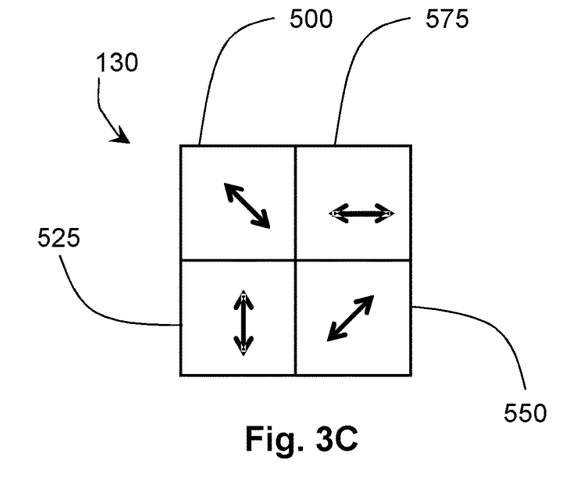

The skilled person may also use trial and error to determine the most appropriate configuration for the polarization modulator. For example, a further modulator 130 is depicted in FIG. 3C. It comprises four distinct and adjacent segments 500, 525, 550, 575 arranged symmetrically as four equal segments of the same square. The segments are numbered counter-clockwise. The first segment 500 provides an area in a beam cross-section with a linear polarization direction in the top left-to-bottom right direction (as schematically depicted), the second segment 525 provides an area in a beam cross-section with a linear polarization direction in the top-to-bottom direction (as schematically depicted), the third segment 550 provides a linear polarization direction in the top right-to-bottom left direction (as schematically depicted), and the fourth segment 575 provides an area in a beam cross-section with a linear polarization direction in the left-to-right direction (as schematically depicted).

When using the modulator of FIG. 3C, the areas in a beam cross-section diagonally opposite to each other have polarization directions which differ by 90 degrees—the corresponding regions in the target area in the skin will also comprise light with polarization directions which differ by 90 degrees. Similarly, the areas in a beam cross-section facing each other have polarization directions which differ by 45 degrees—the corresponding regions in the target area in the skin will also comprise light with polarization directions which differ by 45 degrees.

The most appropriate position in each region to measure the intensity may be routinely determined by the skilled person depending, inter alia, on the position on the body, the dimensions of the incident light beam on the skin and the expected distribution of the collagen. Measurements close to the intersection of the four regions may be more advantageous because it is more likely that the first and second intensity measurements will coincide with the same collagen deposit.

The regions used for the first and second intensity may be predetermined and/or controlled to provide the most accurate measurement depending on, inter alia, the subject of the treatment, the position on the body, the moment in a treatment regime, the pigmentation of the skin, the type of treatment radiation.

It may also be advantageous to simultaneously measure 4 intensities, each corresponding to a measurement in a different region of the target region. The presence of collagen may then be detected by determining the difference between each intensity measurement and an average of the four measurements—in the case of a lack of collagen (or advanced denaturation) the intensity measurements will be substantially the same. If collagen is present, one or more of the intensity measurements will differ substantially from an average of the four measurements.

Based on initial measurements, at least 8 segments may be advantageous. Similarly, 2 to 8 simultaneous intensity measurements may be carried out, each one corresponding to an intensity measurement in a different region of the target area.

The skilled person will also realize that multiple measurements may be performed in each of the regions where measurements are to be carried out. For example, 4 simultaneous measurements may be carried out in each of the regions corresponding to the segments when using the modulators of FIGS. 3A and 3B. Again, this will yield 8 intensity measurements, but the processor may be programmed, for example, to give a higher weighting to any difference between the two intensity measurement groups and a lower weighting to differences between measurements performed in the same region. Multiple intensity measurements may be performed using a detector array, such as a CCD array.

The detection unit 150 may, for example, comprise at least two photodiodes or any other detector able to detect an intensity variation in the reflected light. A single path is depicted in FIG. 1 for the reflected light beam 145, but two separate paths may be provided when two separate detectors are utilized.

The detection unit 150 may also be a detection array, such as a CCD array. The detection unit 150 is connected to a processor and the processor uses the signals from the detection unit 150 to determine the intensity differences between the different regions in the target region. The interaction of polarization incident light beam 140 with birefringent collagen fibers depends on the relative orientation of the polarization direction of the incident polarization light beam 140 with respect to the collagen fiber axis.

Figure 2:
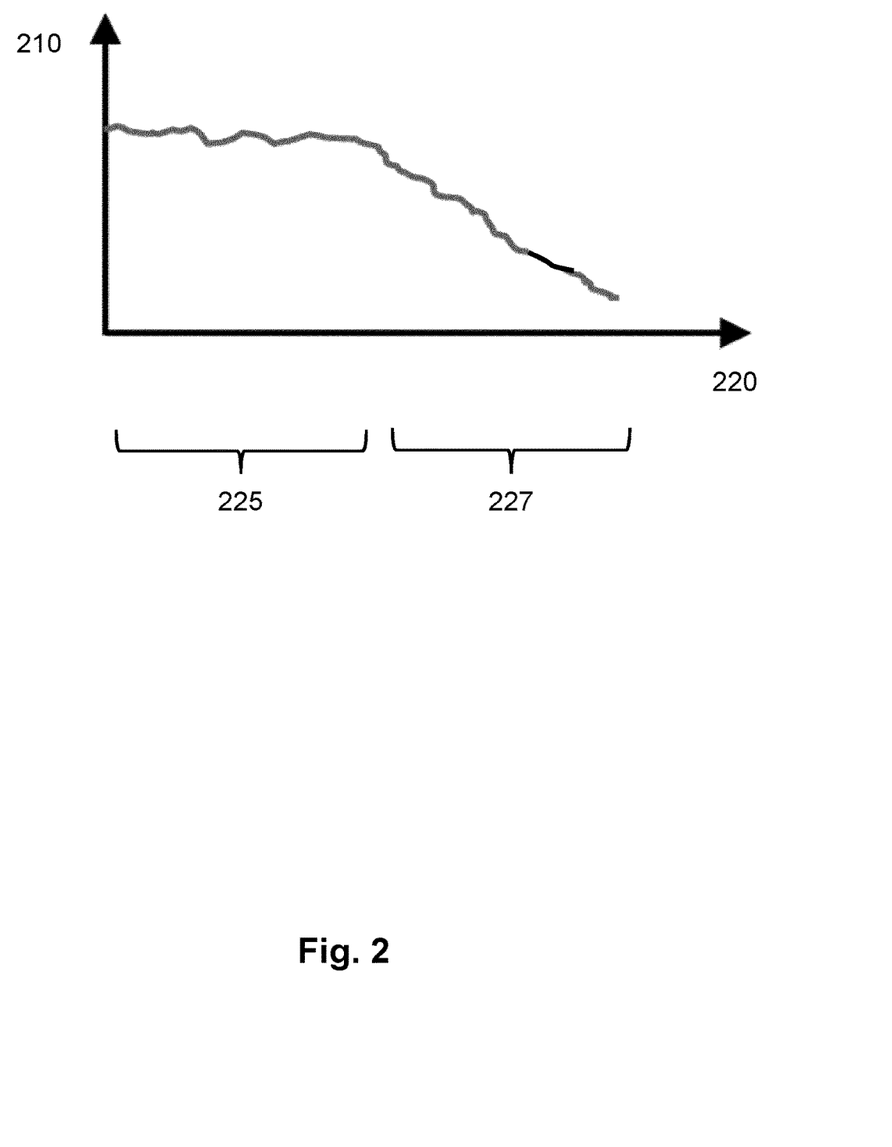
FIG. 2 shows a graph indicating the variation in difference between the intensities of light reflected by different regions of the target position during thermal denaturation of collagen tissue present in the target position, and FIGS. 3A to 3C schematically depict examples of polarization modulators generating spatially modulated linear polarization.

FIG. 2 depicts a graph of the predicted intensity difference along the vertical axis 210 against time along the horizontal axis 220. The intensity difference 210 results from the use of two intensity measurements in regions with polarization directions differing by approximately 45 degrees. Conditions and settings are assumed to be close to optimal, allowing the maximum intensity difference to be obtained between the two regions of measurement.

Before treatment 225, the difference in intensity is substantial (for example, 70-100% of the highest intensity measurement), and substantially constant due to the presence of sufficient collagen. During thermal denaturation of collagen, the birefringence property of collagen is lost, depending on the increase in temperature and this is depicted in FIG. 2 by a steadily decreasing difference in intensity during the treatment 227. Typically, the collagen is heated from approximately 40 degrees C. to at least 65 degrees C., resulting in a loss of birefringence by a factor of 10. At the end of the treatment, the difference is, for example 0-10%.

Collagen denaturation and collagen fiber shrinkage under thermal treatment is described, for example, in "Skin responses to fractional photothermolysis", Laubach, Tannous et al, Lasers Surg. Med., 38: 142-149 (2006). The polarization dependence of the signal on collagen shrinkage is disclosed in, for example, "Collagen denaturation can be quantified in burned human skin using polarization-sensitive optical coherence tomography", Pierce, Sheridan et al, Burns, 30(6), (2004).

The measurement system 110 may further comprise a harmonic separator such as a dichroic beam splitter together with a cut-off filter. This allows measurement of the Second Harmonic Generated SHG light component of the reflected light 145. This may improve the signal to noise ratio in the intensity measurements.

The measurement system 110 may also be comprised in a skin treatment system comprising a treatment source. Such a treatment source may, for example, be an RF radiation source or, for example, a laser source for providing treatment light, typically a pulsed laser beam. The treatment source may, for example, be a Nd:YAG laser with emission at 1064 nm.

The treatment beam path may be completely separate or partially integrated into the beam path of the measurement system. For example, if the treatment source is a laser, the same laser may be used as the light source 120. If the treatment beam is an R.F beam, then the measurement system 110 will be relatively separate from the treatment functions. In such an embodiment, the measurement system 110 may be used as feedback system for measuring an efficacy of the denaturation treatment of collagen fibers by the treatment source. In such a case, the processor may also be connected to the treatment source to control the treatment source, for example, to control the treatment duration or the treatment intensity.

The measurement system 110 may perform real-time measurements continuously during the denaturation treatment, or may perform several measurements during the denaturation treatment which together provide feedback about the denaturation process and the current state of the denaturation treatment.

Additionally or alternatively, the measurement system may be configured and arranged such that the paths of the incident light beam 140 and the reflected light beam 145 partially coincide. This may reduce the dimensions of the measurement system, and allows both the incident light beam 140 and the reflected light beam 145 to the approximately perpendicular to an outer layer of skin.

The invention further relates to a method of collagen denaturation measurement inside skin, the method comprising:
 providing a light source 120;
 configuring and arranging the light source 120 to emit a light beam,
 providing a polarization modulator 130;
 configuring and arranging the polarization modulator 130 to receive the light beam emitted by the light source 120 and to spatially modulate a polarization direction of the light beam emitted by the light source, thereby generating a spatially modulated light beam;
 further configuring and arranging the measurement system to direct the spatially modulated light beam to a target position inside the skin;
 configuring and arranging the polarization modulator to simultaneously provide, in use, at least a first and a second direction of polarization in a cross-section of the spatially modulated light beam in, respectively, at least a first and a second region of the target position, the first and second regions being distinct and the first and second directions of polarization being different from each other,
 providing a detection unit 150;
 configuring and arranging the detection unit 150 to simultaneously detect a first and a second intensity of reflected light 145, the first intensity corresponding to an intensity of light reflected from the first region of the target position 160, and the second intensity corresponding to an intensity of light reflected from the second region of the target position 160; and
providing a processor, coupled to the detection unit 150; and configuring and arranging the processor to determine a difference between the first and the second intensity.

The measurement system 110 described above is configured and arranged to perform the method according to the invention. The detected difference between the intensities of the light reflected from the distinct regions in the target position may be presented to a user as a reliable indication of the status of the collagen denaturation process.

It may also be advantageous for the user if the method further comprises further configuring the processor to determine a degree of collagen denaturation using the difference between the first and the second intensity. This may be used to provide a clear and accurate indication of the denaturation of the collagen, and the end of the treatment.

Although the invention is particularly suited for collagen measurement, the skilled person will be able to configure the invention for use in detecting other skin birefringent structures, such as tendons, elastins, hair, and monitoring the changes in measurement due to the corresponding treatment, such as photoepilation.

It will be appreciated that the invention—especially many of the method steps indicated above—also extends to computer programs, particularly computer programs on or in a carrier, adapted to put the invention into practice. The program may be in the form of a source code, an object code, a code intermediate source and object code such as a partially compiled form, or in any other form suitable for use in the implementation of the method according to the invention.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the system claim enumerating several means, several of these means may be embodied by one and the same item of hardware. The mere fact that certain measures are recited in mutually different dependent claims does not indicate that a combination of these measures cannot be used to advantage.

The invention claimed is:

1. A measurement system for light-based measurement of collagen denaturation inside skin, the measurement system comprising:
   a light source configured and arranged for emitting a light beam,
   a polarization modulator configured and arranged to receive, in use, the light beam emitted by the light source and to spatially modulate a polarization direction of the light beam emitted by the light source, thereby generating a spatially modulated light beam,
   the measurement system being further configured and arranged to direct the spatially modulated light beam to a target position inside the skin,
   wherein the spatially modulated light beam has a spatially modulated polarization direction in a cross-section of the light beam extending perpendicularly to a propagation direction of the light beam,
   the polarization modulator being configured and arranged to simultaneously provide, in use, at least a first and a second direction of polarization in said cross-section of the spatially modulated light beam in, respectively, at least a first and a second region of the target position, the first and second regions being distinct and the first and second directions of polarization being different from each other,
   wherein the polarization directions of the light in the first and second regions in the target position are distinct and predetermined,
   the measurement system further comprising:
   a detection unit configured and arranged to simultaneously detect a first and a second intensity of reflected light, the first intensity corresponding to an intensity of light reflected from the first region of the target position, and the second intensity corresponding to an intensity of light reflected from the second region of the target position; and
   a processor which is coupled to the detection unit and which is configured and arranged to determine a difference between the first and the second intensity, obtained from the first and second regions, respectively.

2. The measurement system according to claim 1, wherein the processor is further configured to determine a degree of collagen denaturation using the difference between the first and the second intensity.

3. The measurement system according to claim 1, wherein the light beam emitted by the light source is linearly polarized.

4. The measurement system according to claim 1, wherein the first and the second direction of polarization each comprise a linear polarization, and an angular difference between the first and the second direction of polarization is approximately equal to 45 degrees.

5. The measurement system according to claim 1, wherein the measurement system further comprises an optical element for focusing the spatially modulated light beam into the target position inside the skin.

6. The measurement system according to claim 1, wherein the first and the second intensity detected by the detection unit correspond to an intensity of a second harmonic generated light (SHG) component reflected from, respectively, the first and the second region of the target position.

7. The measurement system according to claim 6, wherein the detection unit comprises a harmonic separator for separating the reflected second harmonic generated light (SHG) component from the light beam emitted by the light source.

8. The measurement system according to claim 1, wherein a wavelength of the light beam emitted by the light source is in a range from visible light to infrared light.

9. A skin treatment system for denaturation of collagen, wherein the skin treatment system comprises the measurement system according to claim 1.

10. The skin treatment system according to claim 9, wherein the measurement system is configured for measuring the difference between the first and the second intensity before and after a denaturation treatment by the skin treatment system, or for measuring the difference between the first and the second intensity during the denaturation treatment by the skin treatment system to thereby monitor efficacy or progress of the denaturation treatment.

11. A method of collagen denaturation measurement inside skin, the method comprising:
   providing a light source;
   configuring and arranging the light source to emit a light beam;
   providing a polarization modulator;
   configuring and arranging the polarization modulator to receive the light beam emitted by the light source and to spatially modulate a polarization direction of the light beam emitted by the light source, thereby generating a spatially modulated light beam;
   further configuring and arranging the measurement system to direct the spatially modulated light beam to a target position inside the skin;
   providing a detection unit; and
   providing a processor, coupled to the detection unit;
   wherein the spatially modulated light beam has a spatially modulated polarization direction in a cross-section of the light beam extending perpendicularly to a propagation direction of the light beam;
   wherein the polarization directions of the light in the first and second regions in the target position are distinct and predetermined,
   and in that the method further comprises:
   configuring and arranging the polarization modulator to simultaneously provide, in use, at least a first and a second direction of polarization in said cross-section of the spatially modulated light beam in, respectively, at least a first and a second region of the target position, the first and second regions being distinct and the first and second directions of polarization being different from each other;
   configuring and arranging the detection unit to simultaneously detect a first and a second intensity of reflected light, the first intensity corresponding to an intensity of light reflected from the first region of the target position, and the second intensity corresponding to an intensity of light reflected from the second region of the target position; and
   configuring and arranging the processor to determine a difference between the first and the second intensity obtained from the first and second regions, respectively.

12. The method of claim 11, wherein the method further comprises:
   further configuring the processor to determine a degree of collagen denaturation using the difference between the first and the second intensity.

* * * * *